United States Patent [19]

Achini

[11] Patent Number: 4,622,336
[45] Date of Patent: Nov. 11, 1986

[54] 3,3-DIALKYL-AND 3,3-ALKYLENE-INDOLINE DERIVATIVES, PROCESSES FOR THEIR PRODUCTION AND PHARMACEUTICAL COMPOSITIONS COMPRISING THEM

[75] Inventor: Roland Achini, Therwil, Switzerland

[73] Assignee: Sandoz Ltd., Basel, Switzerland

[21] Appl. No.: 458,443

[22] Filed: Jan. 17, 1985

[30] Foreign Application Priority Data

Jan. 21, 1982 [CH] Switzerland .................. 373/82
Jun. 17, 1982 [CH] Switzerland ................. 3745/82

[51] Int. Cl.$^4$ .............. C07D 209/08; C07D 209/54; A61K 31/40
[52] U.S. Cl. .................... 514/409; 548/411; 548/490; 514/415
[58] Field of Search .............. 548/411, 490; 424/274; 514/409, 415

[56] References Cited

U.S. PATENT DOCUMENTS

| 4,159,271 | 6/1979 | Sano et al. | 548/490 |
| 4,216,220 | 8/1980 | Nakagawa et al. | 548/486 |
| 4,255,333 | 3/1981 | Opgenorth et al. | 548/490 |
| 4,307,235 | 12/1981 | Ong et al. | 546/17 |
| 4,345,081 | 8/1982 | Ong et al. | 546/17 |
| 4,408,050 | 10/1983 | Ong et al. | 548/411 |

FOREIGN PATENT DOCUMENTS

| 3143327 | 6/1982 | Fed. Rep. of Germany . | |
| 2245353 | 4/1975 | France . | |
| 48-8777 | 2/1973 | Japan | 548/490 |
| B2033392 | 5/1980 | United Kingdom . | |
| 1603030 | 11/1981 | United Kingdom . | |
| 2087884 | 6/1982 | United Kingdom . | |

OTHER PUBLICATIONS

Z. Obsc. Chim. 23 (1983), P. Kolosow et al, English Edition pp. 1879 to 1883.
Dopp et al, Chem., Ber. 111, 3806 (1978).

Primary Examiner—George F. Lesmes
Assistant Examiner—S. A. Gibson
Attorney, Agent, or Firm—Gerald D. Sharkin; Robert S. Honor

[57] ABSTRACT 3,3-Dialkyl- or 3,3-alkylene-indolines which are unsubstituted at the 1- and 2-positions and which are substituted at the 4- or 6-position by an optionally etherified hydroxy group or substituted at the 5- or 7-position by an etherified hydroxy group, as well as their physiologically-hydrolyzable and -acceptable esters. The said indolines and esters as well as their pharmaceutically acceptable acid addition salts possess analgesic activity.

14 Claims, No Drawings

3,3-DIALKYL-AND 3,3-ALKYLENE-INDOLINE DERIVATIVES, PROCESSES FOR THEIR PRODUCTION AND PHARMACEUTICAL COMPOSITIONS COMPRISING THEM

The present invention relates to novel 3,3-dialkyl- and 3,3-alkylene-indoline derivatives having valuable pharmaceutical properties, processes for their production, pharmaceutical compositions comprising said derivatives and the use of said derivatives as pharmaceuticals.

More particularly the present invention provides a 3,3-dialkyl- or 3,3-alkylene-indoline which is unsubstituted at the 1- and 2-positions and which is substituted at the 4- or 6-position by an optionally etherified hydroxy group or substituted at the 5- or 7-position by an etherified hydroxy group, or a physiologically-hydrolysable and -acceptable ester thereof, in free base or acid addition salt form.

It will be appreciated that in the case of the 3,3-alkylene-indolines of the invention, the alkylene moiety completes a cycloalkyl group with the carbon atom at the 3-position. Such cycloalkyl groups may contain 3 or more, e.g. 3 to 6 carbon atoms, as ring-members. In accordance with the present invention however, 3,3-alkylene-indolines in which the alkylene moiety completes a cyclopropyl group with the carbon atom at the 3-position, e.g. 3,3-ethylene, are generally less preferred.

Alkyl and alkylene moieties at the 3-position may be branched or straight-chained.

The benzene ring of the indolines of the invention may, if desired, bear further substituents, in particular alkyl substituents.

In a preferred embodiment, the present invention provides an indoline of formula I,

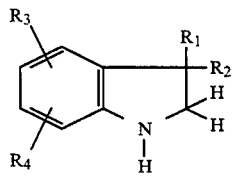

wherein
$R_1$ and $R_2$ are each independently $C_{1-3}$alkyl or together are $-(CH_2)_n-$, wherein n is 2 to 5,
$R_3$ is
(a) hydroxy or $C_{1-6}$alkoxy in the 4- or 6-position, or
(b) $C_{1-6}$alkoxy in the 5- or 7-position and
$R_4$ is hydrogen or $C_{1-3}$alkyl, or a physiologically-hydrolysable and -acceptable ester thereof, in free base or acid addition salt form.

For formula I the following significances or combinations thereof are preferred:
(1) $R_1$ and $R_2$ are each independently $C_{1-3}$alkyl or together are $-(CH_2)_n-$, wherein n is 3 to 5. More preferably $R_1$ and $R_2$ are each independently $C_{1-3}$alkyl. Most preferably $R_1$ and $R_2$ are both methyl.
(2) $R_3$ is
(a) hydroxy or $C_{1-3}$alkoxy, in particular hydroxy, methoxy or ethoxy, more especially ethoxy, in the 4- or 6-position, or
(b) $C_{1-3}$alkoxy, in particular ethoxy, in the 5- or 7-position.
(3) $R_4$ is hydrogen.

Most preferably $R_3$ is in the 5- or 6-position.

One group of compounds in accordance with the present invention comprises the indolines of formula I as defined above, wherein $R_3$ is $C_{1-6}$alkoxy in the 5-position, in free base or acid addition salt form. A further group of compounds in accordance with the present invention comprises the indolines of formula I as defined above, wherein $R_3$ is hydroxy or $C_{1-6}$alkoxy in the 6-position in free base or acid addition salt form.

It will be appreciated that when e.g. $R_1$ and $R_2$ in formula I represent alkyl groups which are different, the indolines of the invention may exist in both racemic as well as optically active form. The present invention is to be understood as including both individual isomeric forms of the compounds defined, as well as mixtures thereof.

The present invention includes the physiologically-hydrolysable and -acceptable esters of indolines of the invention having a hydroxy group in the 4- or 6-position, e.g. the indolines of formula I, wherein $R_3$ is hydroxy. By the term "physiologically-hydrolysable and -acceptable ester" is meant, esters which are hydrolysable under physiological conditions to yield acids which are themselves physiologically acceptable, i.e. which are non-toxic at the desired dosage levels. Such esters include esters with mono- or di-carboxylic acids, in particular carboxylic acids having 2 to 5 carbon atoms.

In addition to the foregoing, the present invention also provides a process for the production of a 3,3-dialkyl- or 3,3-alkylene-indoline as hereinbefore defined, or a physiologically-hydrolysable and -acceptable ester thereof, in free base or acid addition salt form, which process comprises reducing the corresponding 3,3-alkyl- or 3,3-alkylene-2-oxo-indoline in free or N-protected form, and, when the 3,3-dialkyl- or 3,3-alkylene-2-oxo-indoline employed is in N-protected form, removing the N-protecting group, and further, when required, converting an obtained 3,3-dialkyl- or 3,3-alkylene-indoline into another 3,3-dialkyl- or 3,3-alkylene-indoline as hereinbefore defined and/or acylating an obtained 3,3-dialkyl- or 3,3-alkylene-indoline having a hydroxy group in the 4- or 6-position with an appropriate acid to obtain a physiologically-hydrolysable and -acceptable ester thereof, and recovering the product indoline or ester in free base or acid addition salt form.

As a specific embodiment of the above process, the present invention also provides a process for the production of an indoline of formula I as hereinbefore defined, or a physiologically-hydrolysable and -acceptable ester thereof, in free base or acid addition salt form, which process comprises reducing a 2-oxo-indoline of formula II,

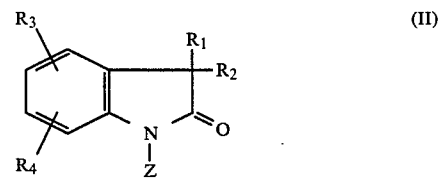

wherein $R_1$, $R_3$, $R_3$ and $R_4$ have the meanings given for formula I and Z is hydrogen or a protecting group, and deprotecting an indoline thus obtained wherein Z is a protecting group, when required trans-alkylating an indoline of formula I thus obtained wherein $R_3$ is $C_{1-6}$ alkoxy, with interim protection of the N-atom, to obtain an indoline of formula I wherein $R_3$ is another $C_{1-6}$ alkoxy group or subjecting an indoline of formula I thus obtained wherein $R_3$ is $C_{1-6}$ alkoxy (in the 4- or 6-position) to ether cleavage to obtain the corresponding indoline wherein $R_3$ is hydroxy and/or acylating an indoline of formula I thus obtained wherein $R_3$ is hydroxy (in the 4- or 6 position), with interim protection of the N-atom, to obtain a physiologically-hydrolysable and -acceptable ester thereof, and recovering the product indoline or ester in free base or acid addion salt form.

The above process may be carried out in accordance with procedures known in the art. Thus reduction, e.g. reduction of the 2-oxo-indoline of formula II may be carried out using any of the reducing agents commonly employed for the conversion of an amide group to an amino group. Particularly suitable reducing agents are metal hydrides, such as $LiAlH_4$, $B_2H_6$ and $AlH_3$. Reduction is suitably carried out in the presence of an inert solvent or diluent such as tetrahydrofuran.

The starting materials of formula II are novel and also form part of the present invention.

Wnen Z in formula II is a protecting group and this is retained in the reduction, or when initially obtained indolines of formula I are acylated or trans-alkylated with interim protection of the N-atom, intermediates of formula III

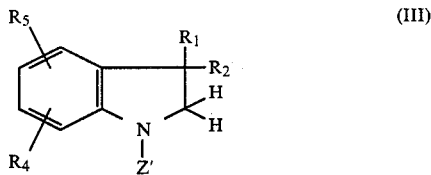

wherein $R_1$, $R_2$ and $R_4$ have the meanings given for formula I, $R_5$ is hydroxy or $C_{1-6}$ alkoxy and $Z'$ is a protecting group, are obtained. These compounds are also novel and form part of the present invention.

Suitable protecting groups for use at the reduction step, e.g. as Z in formula II, include e.g. benzyl. Suitable protecting groups for use when trans-alkylating or acylating initially obtained indolines e.g. of formula I are, for trans-alkylation, acyl groups (in particular acetyl) and, for trans-alkylation or acylation, benzyl. Deprotection may be carried out using any of the techniques known in the art, for example, by hydrolysis or hydrogenolysis. Hydrolysis may be carried out in an acid or alkaline medium, preferably in an aqueous/alkanolic solvent such as $H_2O/CH_3OH$ or $H_2O/C_2H_5OH$ under reflux. Hydrogenolysis, e.g. of benzyl groups, is suitably carried out using a palladium/charcoal catalyst in the presence of an inert solvent or diluent such as methanol, at a temperature of from e.g. 20° to 60° C. at normal or elevated pressure, with passing through of $H_2$.

Ether cleavage of compounds of formula I, wherein $R_3$ is $C_{1-6}$alkoxy in the 4- or 6-position may also be carried out in accordance with standard techniques, for example in the presence of a borotrihalide, preferably $BBr_3$, or of HBr. For ease of reaction, ether cleavage is preferably carried out using compounds of formula I, wherein $R_3$ is 4- or 6-methoxy.

Acylation, e.g. of indolines of formula I, wherein $R_3$ is hydroxy to obtain physiologically-hydrolysable and -acceptable esters may also be carried out in accordance with known techniques, for example by reaction with an appropriate acid halide or acid anhydride, preferably in the presence of an appropriate acid binding or condensation agent, with interim protection of the N-atom, e.g. protection of the N-atom prior to acylation followed by removal of the N-protecting group subsequent to acylation.

Trans-alkylation, e.g. of indolines of formula I wherein $R_3$ is $C_{1-6}$alkoxy may be carried out, e.g. via ether cleavage as hereinbefore described followed by alkylation, e.g. by reaction with an appropriate alkyl halide in the presence of an acidbinding agent. Trans-alkylation is also effected with interim protection of the N-atom, e.g. protection of the N-atom prior to ether cleavage followed by removal of the N-protecting group subsequent to alkylation. Trans-alkylation as aforesaid may be carried out employing indolines of formula I wherein $R_3$ is $C_{1-6}$alkoxy in the 4-, 5-, 6- or 7-position, via intermediates of formula III wherein $R_5$ as hydroxy may be in the 5- or 7-position as well as in the 4- or 6-position.

The product indolines of formula I and their esters may be recovered in free base or acid addition salt form, and obtained free bases can be converted into acid additon salts and vice versa. Suitable acid addition salts for pharmaceutical application include both pharmaceutically acceptable acid addition salts with mineral acids, such as HCl or HBr, as well as with organic acids such as maleic acid.

Optically active isomers of indolines in accordance with the invention, e.g. of indolines of formula I, wherein $R_1$ and $R_2$ are different, may be obtained in accordance with techniques known in the art, e.g. by resolution of racemates or by use of optically active starting materials.

The starting materials of fomula II, wherein $R_3$ is $C_{1-6}$alkoxy, may be produced in accordance with the following reaction scheme, wherein $R_1$, $R_2$ and $R_4$ have the meanings given for formula I; $R_1'$ is $C_{1-3}$alkyl; $R_3'$ is $C_{1-6}$alkoxy, preferably methoxy; $Z'$, $Z''$ and $Z'''$ are protecting groups, whereby $Z''$ is preferably benzyl and $Z'''$ is preferably acyl, especially acetyl; and "Hal" is halogen, especially chlorine or bromine.

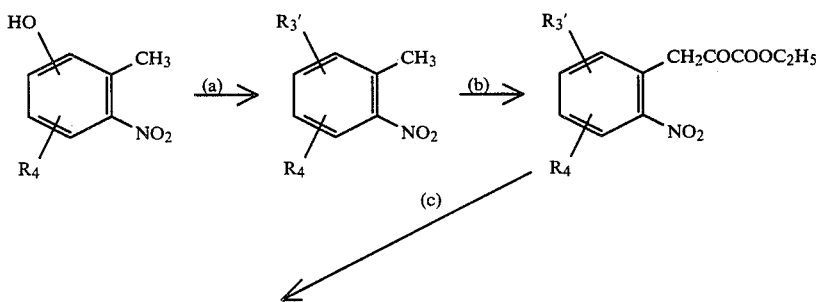

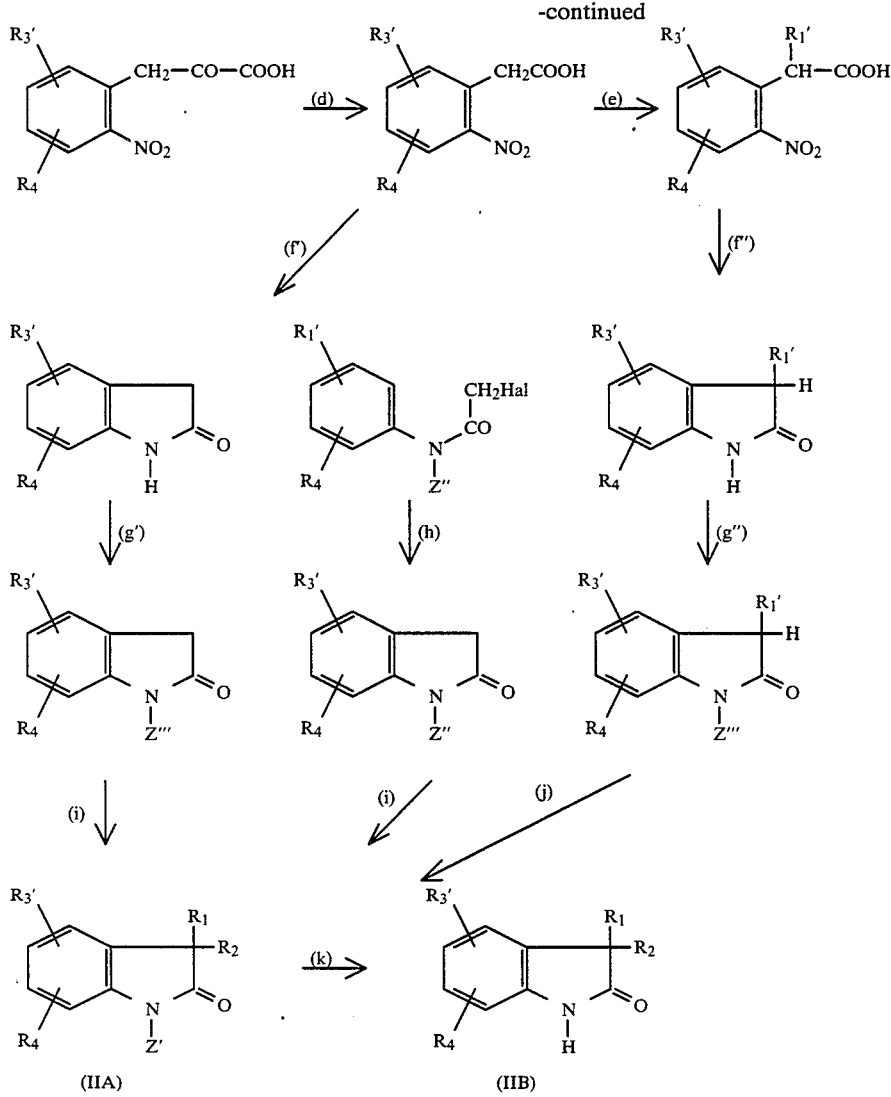

The various reaction steps (a) to (k) may be carried out in accordance with methods known in the art for oxindole synthesis or as hereinafter described in the accompanying examples and involve the following basic procedures: (a) O-alkylation, (b) reaction with diethyl oxalate in the presence of t.$C_4H_9OK$, (c) alkaline hydrolysis, (d) reaction with $H_2O_2$, (e) mono-alkylation, (f') and (f'') catalytic hydrogenation and heating, (g') and (g'') acylation, (h) photochemical cyclisation, (i) di-alkylation (including introduction of alkylene moieties as $R_1$ and $R_2$ together), (j) monoalkylation and (k) de-protection, e.g. by hydrolysis or hydrogenolysis. Synthesis via step (h) is conveniently effected by the method described in Heterocycles 8, 251 (1977).

If compounds of formula IIA or IIB are required in which $R_1$ and $R_2$ are different, the preferred route of synthesis is via steps (e), (f'') and (g'').

Starting materials of formula II, wherein $R_3$ is hydroxy in the 4- or 6-position may be obtained from corresponding compounds of formula IIA or IIB, wherein $R_3'$ is in the 4- or 6-position by ether cleavage, e.g. in accordance with the methods hereinbefore described in relation to formula I. Compounds of formula IIA, wherein $R_3'$ is replaced by hydroxy, may of course be converted into corresponding compounds of formula IIB analogously to step (k). Alternatively, provided $R_3'$ is in the 4- or 6-position, ether cleavage may be carried out subsequent to step (f') or (f'') to yield intermediates subsequent to step (g')/(g'') and (i)/(j) of the formula IV,

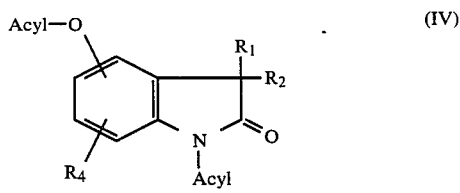

wherein the acyloxy group is in the 4- or 6-position. These may then be hydrolysed to provide 4- or 6-hydroxy analogues of compounds of formula IIB. The compounds of formula IV are also new and also form part of the present invention.

Since $R_3'$ is preferably methoxy, compounds of formula IIA and IIB wherein $R_3'$ is $C_{2-5}$alkoxy are preferably prepared via the $R_3'$=methoxy homologue by trans-etherification as hereinbefore described.

Other known oxindole syntheses in addition to those shown in the foregoing reaction scheme may also be employed. Suitable alternatives are those described in J. Chem. Soc. 1961, 2714; J. Org. Chem. 42, 1340 (1977); and J. Am. Chem. Soc. 96, 5508–5512 (1974).

Starting materials required for the production of further 3,3-dialkyl- or 3,3-alkylene-indolines in accordance with the present invention may be prepared analogously to the procedures described above for the preparation of compounds of formula II.

The following examples are illustrative of the above described processes. All parts indicated are by weight. The following abbreviations are used:
THF=Tetrahydrofuran
HMPT=Hexamethylphosphoric triamide.

EXAMPLE 1

(a) 3,3-Dimethyl-5-methoxy-indoline:

11.8 ml 100% sulfuric acid dissolved in 250 ml THF are added at $-5°$ C. with stirring and under an atmosphere of nitrogen to a suspension of 16.8 g $LiAlH_4$ in 560 ml THF. Stirring is continued at the same temperature and a solution of 28.0 g 3,3-dimethyl-5-methoxy-indolin-2-one in 250 ml THF are added drop-wise over 40 minutes at $0°$ C. After stirring for a further 18 hours at room temperature, saturated aqueous sodium sulfate solution is added and the obtained precipitate filtered off. The filtrate is evaporated and the residue dissolved in 2N methanolic HCl. After concentration and re-crystallisation from ethanol, the title compound is obtained as the hydrochloride: M.P.=$169°$–$170°$ C.

The starting material for the above process is obtained as follows:

(b) 1-Acetyl-5-methoxy-indolin-2-one:

120.0 g 5-methoxy-indolin-2-one in 1.2 l acetic anhydride are heated for 4 hours under reflux. After evaporation the residue is shaken with aqueous $NaHCO_3/CH_2Cl$ and the organic phase is separated, dried over $MgSO_4$, evaporated and re-crystallised from ether to yield the title compound: M.P.=$139°$–$140°$ C.

(c) 3,3-Dimethyl-5-methoxy-indolin-2-one:

19.3 ml of a 2.34 molar solution of butyllithium in cyclohexane are added with stirring at $0°$ C. under a nitrogen atmosphere to a solution of 6.35 ml diisopropylamine in 45 ml THF and 7.9 ml HMPT. The mixture is stirred for a further 30 minutes at $0°$ C., cooled to $-78°$ C., and 3.0 g of the product of step (a) dissolved in 20 ml THF are then added. After stirring for a further hour at $-78°$ C., 2.0 ml methyliodide are added and the reaction mixture allowed to rise to room-temperature with continuous stirring. The mixture is rendered alkaline by the addition of 2N NaOH and stirred for a further 15 hours at room temperature. Readily-volatile solvent components are evaporated under vacuum and the obtained mixture extracted with ethylacetate. The organic phase is evaporated under vacuum (to remove HMPT) and the residue re-crystallised from ethyl-ether/petroleum-ether to yield the title compound: M.P.=$146°$–$147°$ C. Additional product may be obtained from the mother-liquor chromatographically using 30 parts silica gel and $CH_2Cl_2/CH_3OH$ (99:1) as eluant.

EXAMPLE 2

(a) 3,3-Dimethyl-5-isopropoxy-indoline:

The title compound is produced analogously to example 1 (a). M.P. for the hydrochloride=$210°$–$212°$ C. The required starting material is obtained as follows:

(b) 1-Acetyl-5-isopropoxy-indolin-2-one:

Obtained from 5-isopropoxy-indolin-2-one analogously to example 1 (b): recovered as an oil.

(c) 3,3-Dimethyl-5-isopropoxy-indolin-2-one (starting material):

Obtained from the product of step (b) analogously to example 1 (c): M.P.=$134°$–$135°$ C. The starting material is alternatively produced from the product of example 1 by the following procedure:

(d) 3,3-Dimethyl-5-hydroxy-indolin-2-one:

25.9 g 3,3-Dimethyl-5-methoxy-indolin-2-one and 125 ml 48% aqueous HBr are heated for 2 hours under reflux. After cooling, the pH is adjusted to 8 by the addition of NaOH and aqueous $Na_2CO_3$ and the solution extracted with ethyl acetate. The title compound is obtained after evaporation of the organic phase and re-crystallisation from $CH_3OH$/ethyl-ether: M.P.=$254°$–$255°$ C.

(e) 3,3-Dimethyl-5-isopropoxy-indolin-2-one:

5.0 g of the product of step (d), 23.4 g $K_2CO_3$ and 169 ml isopropyl iodide in 150 ml acetone are heated for 24 hours under reflux, and the obtained reaction mixture filtered, evaporated, chromatographed on 20 parts silica gel with $CH_2Cl_2/CH_3OH$ (99:1) as eluant and finally re-crystallised from $CH_2Cl_2$/hexane to yield the title compound: M.P.=$134°$–$135°$ C.

EXAMPLE 3

(a) 3,3-Dimethyl-5-ethoxy-indoline:

The title compound is produced analogously to example 1(a). M.P. for the hydrochloride=$178°$–$179°$ C. following sublimation at $120°$/0.005 mm. The required starting material is obtained as follows:

(b) 1-Acetyl-5-ethoxy-indolin-2-one:

Obtained from 5-ethoxy-indolin-2-one analogously to example 1 (b): M.P.=$101°$–$103°$ C.

(c) 3,3-Dimethyl-5-ethoxy-indolin-2-one (starting material):

Obtained from the product of step (b) analogously to example 1 (c): M.P.=$162°$–$163°$ C.

The starting material is alternatively produced from the product of example 2 (d) analogously to the process of example 2 (e).

EXAMPLE 4

(a) 5-Methoxy-3,3,7-trimethyl-indoline:

The title compound is produced analogously to example 1 (a). The hydrochloride is recovered as an amourphous powder. The required starting material is obtained as follows:

(b) 3(5-Methoxy-3-methyl-2-nitrophenyl)-2-oxo-propionic acid:

2.0 g 4-Methoxy-2,6-dimethyl-nitrobenzene dissolved in 4 ml diethyl oxalate are added to a suspension of 2.47 g potassiumt.butylate in 12 ml diethyl oxalate with stirring at room temperature. Stirring is continued for 15 hours and the reaction mixture combined with water, acidified with acetic acid and extracted with $CH_2Cl_2$. The organic phase is washed with $Na_2CO_3$, dried over $MgSO_4$ and evaporated. The residue is stirred for 2 hours at room temperature with 50 ml ethyl-ether and 50 ml 1N NaOH. The aqueous phase is acidified and extracted with $CH_2Cl_2$ to yield the title compound: M.P.=$150°$–$151°$ C.

(c) 5-Methoxy-3-methyl-2-nitrophenylacetic acid:

3.35 ml 6% aqueous $H_2O_2$ are added with stirring at $20°$–$25°$ C. to a solution of 62.6 g of the product of step (b) and 11.8 g NaOH in 700 ml water. The reaction mixture is stirred for a further 2 hours at room temperature. After acidification with dilute HCl the title compound crystallises out under ice-cooling: M.P.=146°–148° C.

(d) 5-Methoxy-7-methyl-indolin-2-one:

The product of step (c) is hydrogenated using 10% palladium on charcoal as catalyst over a 48 hour period under normal pressure and with heating in THF and refluxing in dioxane for 15 hours. The title compound is recovered from the reaction system and re-crystallised from $CH_3OH/CH_2Cl_2$: M.P.=217°–218° C.

(e) 1-Acetyl-5-methoxy-7-methyl-indolin-2-one:

The title compound is obtained from the product of step (d) analogously to example 1 (b): M.P.=116°–117° C.

(f) 5-Methoxy-3,3,7-trimethyl-indolin-2-one (starting material):

The title compound is obtained from the product of step (e) analogously to example 1 (c): M.P.=179°–180° C.

EXAMPLE 5

(a) 5-Ethoxy-3,3,7-trimethyl-indoline:

The title compound is produced analogously to example 1 (a). M.P. for the hydrochloride=166°–167° C. The required starting material is obtained as follows:

(b) 5-Hydroxy-3,3,7-trimethyl-indolin-2-one:

Obtained from the product of example 4 (f) analogously to example 2(d): M.P.=209°–210° C.

(c) 5-Ethoxy-3,3,7-trimethyl-indolin-2-one (starting material):

Obtained from the product of step (b) analogously to example 1 (e): M.P.=158°–159° C.

EXAMPLE 6

(a) 3,3-Dimethyl-6-ethoxy-indoline:

The title compound is obtained analogously to example 1 (a): M.P. for the hydrobromide=154°–155° C. The required starting material is obtained as follows:

(b) 1-Acetyl-6-acetyloxy-indolin-2-one:

67.9 g 6-hydroxy-indolin-2-one and 670 ml acetic acid anhydride are heated under reflux for 2 hours. The obtained reaction mixture is evaporated, the residue taken up 2x in toluene, evaporated and re-crystallised from $CH_2Cl_2$/ethyl-ether to yield the title compound: M.P.=150°–152° C.

(c) 3,3-Dimethyl-6-hydroxy-indolin-2-one:

369 ml of a 2.34 molar solution of butyl-lithium in cyclohexane are added with stirring under a nitrogen atmosphere at 0° C. to a solution of 127 ml di-iso-propylamine in 450 ml THF. The obtained mixture is stirred for a further 30 minutes at 0° C. and cooled to −78° C., whereupon 41.9 g of the product of step (b) dissolved in 600 ml THF are added drop-wise. After stirring for 1 hour at −78° C., 55.8 ml methyl iodide are added at the same temperature. The temperature of the reaction mixture is allowed to rise with stirring to room temperature, rendered alkaline by the addition of 2N aqueous NaOH and stirred for a further 15 hours at room temperature. Readily volatile organic soluents are evaporated off under vacuum. The title compound is obtained after extraction with ethyl acetate, evaporation of the organic phase under vacuum and re-crystallisation from $CH_3OH$/ethyl-ether: M.P.=232°–234° C.

(d) 3,3-Dimethyl-6-ethoxy-indolin-2-one (starting material):

8.3 g of the product of step (c), 38.8 g $K_2CO_3$ and 22.7 ml ethyl iodide in 300 ml acetone are heated under reflux for 24 hours. The obtained reaction mixture is filtered and evaporated and the residue taken up in ethyl acetate. The title compound is obtained after shaking 2x with water, drying over $Mg_2SO_4$, concentration and dilution with ethyl-ether: M.P.=175°–176° C.

EXAMPLE 7

3,3-Dimethyl-6-hydroxy-indoline:

The title compound is obtained analogously to example 1 (a), starting from the product of example 6 (c). M.P. for the hydrochloride=214°–216° C.

EXAMPLE 8

(a) 3,3-Dimethyl-5-ethoxy-indoline:

2.0 g 1-Acetyl-3,3-dimethyl-5-ethoxy-indoline are heated under reflux for 15 hours with 10 ml 95% $C_2H_5OH$ and 10 ml conc. HCl. The title compound crystallises out as the hydrochloride on cooling and concentration of the reaction medium: M.P.=178°–179° C., following sublimation at 120° C./0.005 mm. The starting material is obtained as follows:

(b) 1-Acetyl-3,3-dimethyl-5-methoxy-indoline:

13.3 g 3,3-Dimethyl-5-methoxy-indoline [c.f. example 1 (a)], 100 ml acetic acid and 35 ml acetic anhydride are heated under reflux for 4 hours. After evaporation, the residue is taken up in aqueous $Na_2CO_3$ and extracted with $CH_2Cl_2$. The title compound is obtained following re-crystallisation from ethyl-ether/petroleum ether: M.P.=88°–89° C.

(c) 1-Acetyl-3,3-dimethyl-5-hydroxy-indoline:

98 ml of a 1N solution of $BBr_3$ in $CH_2Cl_2$ are added with stirring at −70° C. to a solution of 9.77 g of the product of step (b) in 100 ml $CH_2Cl_2$. The reaction mixture is allowed to stand for 2 hours at room temperature and is then poured onto water. The organic phase is separated off and the aqueous phase extracted with $CH_2Cl_2$. The title compound is obtained after combination and evaporation of the organic phases and re-crystallisation from $CH_3OH$/ethyl-ether: M.P.=169°–170° C.

(d) 1-Acetyl-3,3-dimethyl-5-ethoxy-indoline (starting material):

6.0 g of the product of step (c), 12.2 g $K_2CO_3$ and 7.0 ml ethyl iodide in 150 ml acetone are heated with stirring under reflux for 15 hours. After addition of a further 7.0 ml ethyl iodide and refluxing for a further 5 hours, the reaction mixture is cooled, filtered and the filtrate evaporated. The residue is filtered over 10 parts silica gel, using $CH_2Cl_2$ as eluant and re-crystallisation effected from ethyl-ether/petroleum-ether to yield the title compound: M.P.=103°–104° C.

EXAMPLE 9

(a) 3,3-Dimethyl-5-isopropoxy-indoline:

The title compound is obtained analogously to example 8 (a). M.P. for the hydrochloride=210°–213° C. The required starting material:

(b) 1-Acetyl-3,3-dimethyl-5-isopropoxy-indoline is obtained analogously to example 8(d), starting from the product of example 8 (c): M.P.=86°–87° C.

EXAMPLE 10

(a) 3,3-Dimethyl-6-isopropyloxy-indoline:

The title compound is produced analogously to example 1 (a): M P. for the hydrochloride=170°–172°. The required starting material:

(b) 3,3-Dimethyl-6-isopropyloxy-indolin-2-one is obtained from the product of example 6 (c) analogously to example 2 (e): M.P.=119°–120° C.

EXAMPLE 11

(a) 6-Ethoxy-3,3,5-trimethyl-indoline:

The title compound is produced analogously to example 1 (a): M.P. for the hydrochloride=125°–126° C. The required starting material is obtained as follows:

(b) 6-Hydroxy-3,3,5-trimethyl-indolin-2-one:

Obtained by cyclisation of N-α-bromo-isobutyryl-(3-hydroxy-4-methyl-phenyl)-amine in the presence of AlCl$_3$: M.P.=200°–210°.

(c) 6-Ethoxy-3,3,5-trimethyl-indolin-2-one (starting material):

Obtained from the product of step (b) analogously to example 2 (e): M.P.=168°–170°.

EXAMPLE 12

(a) 3,3-Dimethyl-7-ethoxy-indoline:

The title compound is obtained analogously to example 1 (a), but employing B$_2$H$_6$ as reducing agent: M.P. for the hydrochloride=201° C. The required starting material is obtained as follows:

(b) 1-Acetyl-7-methoxy-indolin-2-one:

Obtained from 7-methoxy-indolin-2-one analogously to example 1 (b): M.P.=88°.

(c) 3,3-Dimethyl-7-methoxy-indolin-2-one:

Obtained from the product of step (b) analogously to example 1 (b): M.P.=134°.

(d) 3,3-Dimethyl-7-hydroxy-indolin-2-one:

Obtained from the product of step (c) analogously to example 2 (d): M.P.=215°.

(e) 3,3-Dimethyl-7-ethoxy-indolin-2-one (starting material):

Obtained from the product of step (d) analogously to example 2(e): M.P.=126°.

EXAMPLE 13

(a) 3,3-Dimethyl-4-ethoxy-indoline: .

The title compound is obtained analogously to example 1 (a): M.P. for the hydrochloride=240°–242° C. The required starting material is obtained as follows:

(b) 1-Acetyl-4-acetyloxy-indolin-2-one:

Obtained from 4-hydroxy-indolin-2-one analogously to example 6 (b): M.P.=150°–151° C.

(c) 3,3-Dimethyl-4-hydroxy-indolin-2-one:

Obtained from the product of step (b) analogously to example 6 (c): M.P.=220°–222° C.

(d) 3,3-Dimethyl-4-ethoxy-indolin-2-one (starting material):

Obtained from the product of step (c) analogously to example 6 (d): M.P.=144°–146° C. The 3,3-dialkyl- and 3,3-alkylene-indolines of the present invention, in particular the indolines of formula I as hereinbefore defined, as well as the physiologically-hydrolysable and -acceptable esters thereof and the pharmaceutically acceptable acid addition salts of said indolines and esters, possess valuable pharmaceutical, in particular analgesic, properties as indicated by activity in e.g.:

(A) the arthritis pain test in the rat [based on the method of A. W. Pircio et al., Eur. J. Pharmacol., 31, 207–215 (1975)] at dosages of from 3 to 50 mg/kg p.o.; and (B) the Randall-Selitto test on the inflamed rat-hind-paw [Arch. Int. Pharmacodyn. 61, 409–419 (1957)] at dosages of from 20 to 200 mg/kg p.o..

The said indolines, esters and salts are accordingly useful as analgesic agents, e.g. in the treatment of pain. For this use the dosage will, of course, vary depending on e.g. the particular compound employed, the mode of administration, the condition to be treated (e.g. the aetiology of the pain to be treated) and the effect desired. However, in general, satisfactory results are obtained on administration at daily dosages of from about 1 to about 200 mg/kg body weight conveniently administered in divided dosages 2 to 4x daily or in sustained release form. For larger mammals, the total daily dosage is in the range of from about 100 to 500 mg and suitable dosage forms, e.g. for oral administration contain from about 25 to about 250 mg of active ingredient in free base or pharmaceutically acceptable acid addition salt form together with a pharmaceutically acceptable diluent or carrier therefor. As already indicated the daily dosages suitable for any particular compound will depend on a number of factors, including its relative potency of activity. Results obtained in tests A and B above for preferred compounds of the present invention, namely the products of examples 1 and 6, compared with results obtained for the known analgesic paracetamol are:

| | COMPOUND | ED$_{50}$ (mg/kg p.o.) TEST A | TEST B |
| --- | --- | --- | --- |
| I | 3,3-Dimethyl-5-ethoxy-indoline (example 3) | 18 | 133 |
| II | 3,3-Dimethyl-6-ethoxy-indoline (example 6) | 7 | 78 |
| III | Paracetamol | 174 | 203 |

An indicated daily dosage for compounds I and II would accordingly be of the order of from about ½ to about 1/10, and from about ⅓ to about 1/25 respectively of the daily dosage applicable in the case of paracetamol.

In accordance with the foregoing the present invention also provides (i) A 3,3-dialkyl- or 3,3-alkylene-indoline as hereinbefore defined, in particular an indoline of formula I as hereinbefore defined, or a physiologically-hydrolysable and -acceptable ester thereof, in free base or pharmaceutically acceptable acid addition salt form for use as a pharmaceutical, e.g. for use as an analgesic;

(ii) A method of treating (e.g. alleviating) pain in a subject in need of such treatment, which method comprises administering to said subject an analgesically effective amount of an indoline or ester as specified under (i) above in free base or pharmaceutically acceptable acid addition salt form; as well as (iii) A pharmaceutical composition comprising an indoline or ester as specified under (i) above in free base or pharmaceutically acceptable acid addition salt form, together with a pharmaceutically acceptable diluent or carrier therefor.

Pharmaceutical compositions in accordance with (iii) above may be prepared employing conventional techniques known in the galenic art. Suitable galenic forms for administration include e.g. tablets and liquid preparations.

I claim:

1. A method of treating pain in a subject in need of such treatment which comprises administering to said subject an analgesically effective amount of an indoline of formula I:

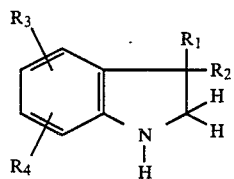

wherein

R₁ and R₂ are each independently $C_{1-3}$alkyl or together are —$(CH_2)_n$—, wherein n is 2 to 5, R₃ is (a) hydroxy or $C_{1-6}$alkoxy in the 4- or 6-position, or (b) $C_{1-6}$alkoxy in the 5- or 7-position and R₄ is hydrogen or $C_{1-3}$alkyl, or a physiologically-hydrolysable and -acceptable ester thereof, or of a pharmaceutically acceptable acid addition salt thereof.

2. A method according to claim 1 wherein the compound of formula I represents 3,3-dimethyl-6-ethoxy-indoline or a pharmaceutically acceptable acid addition salt thereof.

3. A pharmaceutical composition useful in treating or preventing pain comprising an analgesically effective amount of indoline as claimed in claim 1, or a pharmaceutically acceptable acid addition salt thereof, together with a pharmaceutically acceptable diluent or carrier therefor.

4. An indoline which is 3,3-dimethyl-5-ethoxy-indoline, or a pharmaceutically acceptable acid addition salt thereof.

5. An indoline which is 3,3-dimethyl-6-ethoxy-indoline, or a pharmaceutically acceptable acid addition salt thereof.

6. A compound which is 3,3-dimethyl-7-ethoxy-indoline or a pharmaceutically acceptable acid addition salt thereof.

7. A compound which is 3,3-dimethyl-4-ethoxy-indoline or a pharmaceutically acceptable acid addition salt thereof.

8. A compound which is 3,3-dimethyl-6-hydroxy-indoline or a pharmaceutically acceptable acid addition salt thereof.

9. A compound which is 3,3-dimethyl-6-iso-propyloxy-indoline or a pharmaceutically acceptable acid addition salt thereof.

10. A compound which is 6-ethoxy-3,3,5-trimethyl-indoline or a pharmaceutically acceptable acid addition salt thereof.

11. A compound which is 3,3-dimethyl-5-methoxy-indoline or a pharmaceutically acceptable acid addition salt thereof.

12. A compound which is 3,3-dimethyl-5-iso-propyloxy-indoline or a pharmaceutically acceptable acid addition salt thereof.

13. A compound which is 5-methoxy-3,3,7-trimethyl-indoline or a pharmaceutically acceptable acid addition salt thereof.

14. A compound which is 5-ethoxy-3,3,7-trimethyl-indoline or a pharmaceutically acceptable acid addition salt thereof.

* * * * *